United States Patent
Klein et al.

(10) Patent No.: US 9,643,901 B2
(45) Date of Patent: May 9, 2017

(54) METHOD AND DEVICE FOR GENERATING AN ALKENE

(71) Applicant: LINDE AKTIENGESELLSCHAFT, Munich (DE)

(72) Inventors: Bernd Klein, Munich (DE); Thomas Trott, Munich (DE)

(73) Assignee: LINDE AKTIENGESELLSCHAFT, Munich (DE)

( * ) Notice: Subject to any disclaimer, the term of this patent is extended or adjusted under 35 U.S.C. 154(b) by 189 days.

(21) Appl. No.: 14/334,146

(22) Filed: Jul. 17, 2014

(65) Prior Publication Data
US 2015/0025290 A1 Jan. 22, 2015

(30) Foreign Application Priority Data
Jul. 18, 2013 (DE) .................. 10 2013 011 984

(51) Int. Cl.
*C07C 5/333* (2006.01)
*C07C 5/327* (2006.01)
*B01D 53/26* (2006.01)

(52) U.S. Cl.
CPC ............. *C07C 5/333* (2013.01); *C07C 5/327* (2013.01); *B01D 53/261* (2013.01); *B01D 2256/24* (2013.01); *B01D 2257/80* (2013.01)

(58) Field of Classification Search
CPC ......... C07C 5/327; C07C 5/333; C07C 11/06; C07C 5/23; C07C 5/36; B01D 53/261; B01D 2257/80; B01D 2256/24; F25J 3/06; C10G 9/00
USPC ....... 585/2, 3, 655, 809; 62/11, 23; 208/101, 208/102, 103
See application file for complete search history.

(56) References Cited

U.S. PATENT DOCUMENTS 5,414,168 A * 5/1995 Scott .................. C01B 3/52
208/101

* cited by examiner

*Primary Examiner* — Sharon Pregler
(74) *Attorney, Agent, or Firm* — Millen, White, Zelano, Branigan, P.C.

(57) ABSTRACT

The invention relates to a method for generating an alkene, in which a hydrocarbon-comprising feed material is subjected to a dehydrogenation and a product material comprising at least one alkene is generated. A gas stream coming from an adsorber is cooled by a gas stream which comprises the feed material, and the gas stream coming from the adsorber is cooled by a condensed component of the gas stream coming from the adsorber in a first cooling phase. Feed material is cooled in a second cooling phase by a condensed component of the gas stream coming from the adsorber. The flow of the condensed component of the gas stream coming from the adsorber, fed to the first and/or second cooling phase, is varied depending on the temperature of the gas stream leaving the first cooling phase which comprises the feed material and which is fed to the dehydrogenation.

16 Claims, 1 Drawing Sheet

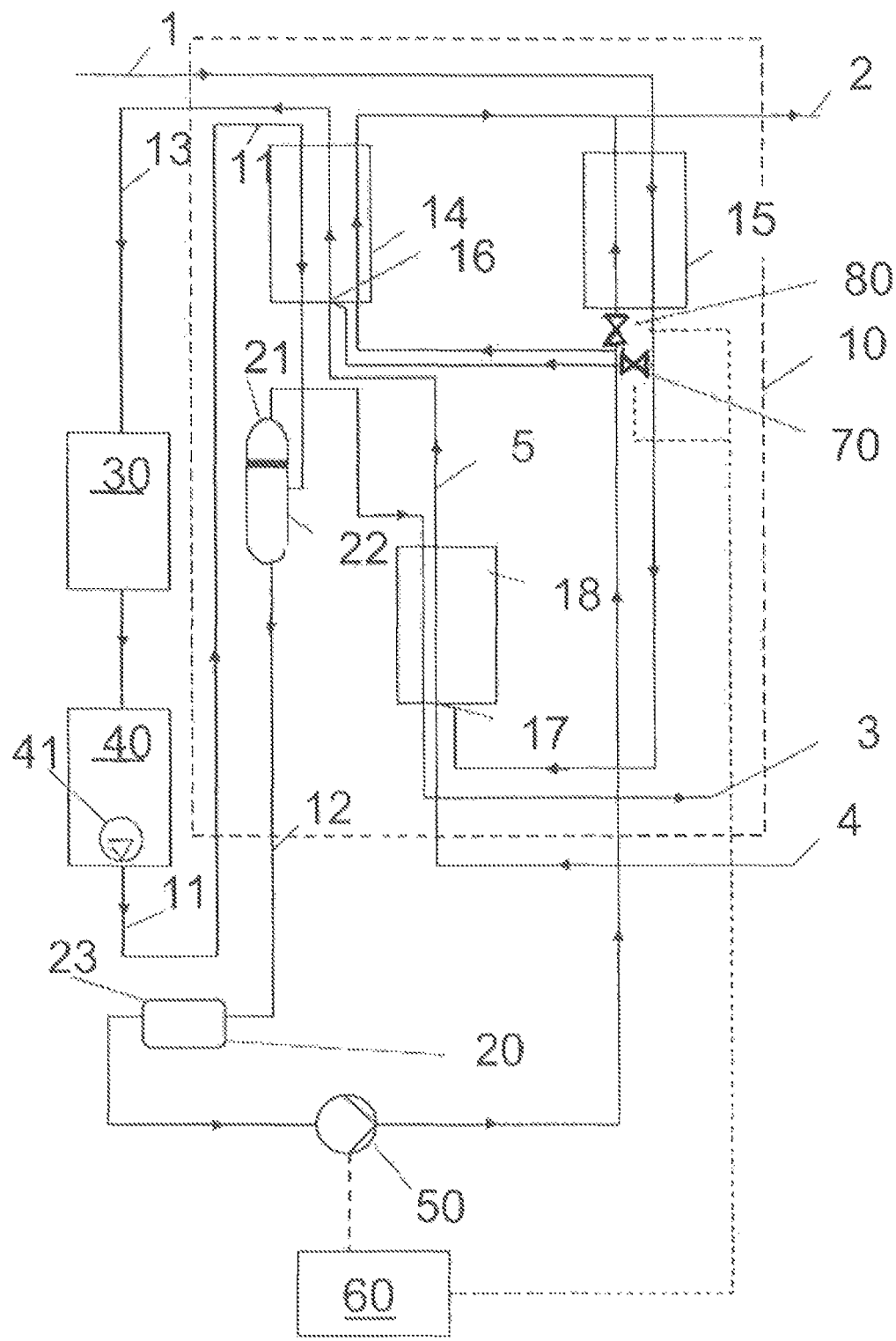

METHOD AND DEVICE FOR GENERATING AN ALKENE

The present invention relates to a method for generating an alkene and also a device for carrying out the method.

Alkenes, which are also known under the name olefins, are chemical compounds of the group of the aliphatic hydrocarbons which have at least one carbon double bond at any position in the molecule. Alkenes can be produced by dehydrogenation of alkanes.

A known alkene is, for example, propene (also called propylene), which can be produced from propane by dehydrogenation. Such a dehydrogenation may be effected in what is termed the Oleflex process. In such a dehydrogenation process, in the course of a cryogenic separation of a gas stream coming from the dehydrogenation reactor, a hydrogen or hydrogen-rich gas stream, and also a hydrocarbon-rich liquid end product are generated. In the same system, a feed material stream is also mixed with what is termed a recycled gas stream which, for example, likewise substantially comprises hydrogen, to give what is termed a combined gas stream.

From the gas exiting from the dehydrogenation reactor, water is removed via drying in an adsorber.

Usually used adsorbers need to be regenerated in order to ensure a sufficient drying capacity. Such regenerations, however, lead to fluctuations in the temperature, the flow amount and/or the hydrogen content of the dehydrogenated gas, and therefore also the molecular weight of the dehydrogenated gas.

The dehydrogenated gas is cooled in insulated surroundings, what is termed the "cold box", and the hydrocarbons are condensed out which can then be separated off from the hydrogen-rich fraction. Owing to the heat liberated from the dehydrogenated gas during cooling or condensation, the two-phase combined gas stream (i.e., the feed material stream mixed with the recycled gas stream) can be vaporized and introduced into the dehydrogenation reactor as a gas stream.

In this case the physical properties of the combined gas stream must be kept as constant as possible. Owing to the heating of the combined gas stream or of the feed stream via the fluid leaving the adsorber, owing to the fluctuations of the operation of the adsorber, it is no longer ensured that the combined gas stream has constant physical parameters. However, the fluctuations in adsorber operation occur only within a relatively short time period during the adsorber regeneration.

An object of the present invention is therefore to provide a method and a device by means of which, in a simple, inexpensive and reliable manner, the temperature-control of the feed material, or of a stream comprising the feed material, is ensured in such a manner that the feed material reaching the dehydrogenation reactor, or the stream comprising the feed material reaching the dehydrogenation reactor, is constant in the important physical parameters thereof.

Upon further study of the specification and appended claims, other objects, aspects and advantages of the invention will become apparent.

These objects are achieved by a method according to the invention for generating an alkene, in which a hydrocarbon-comprising feed material is subjected to a dehydrogenation and a product material comprising at least one alkene is generated, comprises according to the invention the following steps:

cooling a gas stream coming from an adsorber by a gas stream which comprises the feed material in a first cooling phase, and cooling the gas stream coming from the adsorber by a condensed component of the gas stream coming from the adsorber in the first cooling phase, and cooling the feed material in a second cooling phase by a condensed component of the gas stream coming from the adsorber.

Further advantageous embodiments of the method according to the invention are described herein.

According to the invention it is provided that the flow volume of the condensed component of the gas stream coming from the adsorber that is fed to the first cooling phase and/or the second cooling phase, is varied in dependence on the temperature of the gas stream leaving the first cooling phase, that is the gas stream which comprises the feed material and which is fed to the dehydrogenation In particular, this method may be employed for generating an alkene or olefin such as, e.g., propene, or a propane-propene mixture. Such an alkene or such a mixture, after the production described, is then fed to what is termed a C3 splitter.

The gas stream coming from the adsorber is what is termed a cold box vapor feed, i.e. a gas volumetric stream comprising the feed material which has previously flowed through the dehydrogenation reactor for dehydrogenation of hydrocarbons in the feed material and an adsorber for removal of water or for drying the fluid coming from the dehydrogenation reactor.

In addition, it is advantageously provided that the feed material stream is mixed with a recycled gas stream to form a combined gas stream. The recycled gas stream is preferably hydrogen, or a gas mixture substantially containing hydrogen, which hydrogen, or which gas mixture is formed as a by-product of the product material.

The method according to the invention is advantageously formed, in particular, when in the second cooling phase, the feed material is cooled by transfer of cold from the condensed component of the gas stream coming from the adsorber to a feed material stream.

For the purpose of cooling, here, for simple configuration of the method, transfer of cold from the condensed component of the gas stream coming from the adsorber to the gas stream coming from the adsorber is provided in a first heat exchanger. The transfer of cold from the condensed component of the gas stream coming from the adsorber to the feed material stream proceeds in this case in a second heat exchanger.

The transfer of cold from the condensed component of the gas stream coming from the adsorber to the gas stream coming from the adsorber and/or the transfer of cold from the gas stream which comprises the feed material to the gas stream coming from the adsorber is carried out in dependence on the temperature of the gas stream leaving the first cooling phase, which gas stream comprises the feed material and is fed to the dehydrogenation. The method for generating an alkene can be constructed here in such a manner that the first cooling phase and the second cooling phase run simultaneously at least for periods of time.

For the purpose of control of the cooling it is preferably provided that, downstream of the adsorber, at least one parameter of the gas stream coming from the adsorber is determined, this parameter is compared with a permissible limiting value range and, in the event of deviation of the determined parameter from the limiting value range, at least one parameter of the stream of the condensed component of the gas stream coming from the adsorber is varied. The parameter of the material or of the volumetric stream of the gas stream coming from the adsorber is preferably determined in the first heat exchanger. A parameter that is to be determined can be, in particular, a physical parameter such as, e.g., the temperature or the velocity of the gas stream. The limiting value range, with which the parameter is compared, is a parameter limiting value range which is defined according to refrigeration performance requirement and is preferably stored in a retrievable manner. As a result, in a simple manner, any fluctuations affected by the adsorber with regard to temperature, mass, flow volume and/or the hydrogen content of the gas stream coming from the adsorber and the refrigeration performance thereof resulting therefrom are compensated for.

Advantageously, it is provided that the condensed component of the gas stream coming from the adsorber is stored in a storage appliance and from there is fed to the first and/or second cooling phase according to refrigeration performance requirement. That is to say that the feed from the storage appliance proceeds in dependence on the temperature of the gas stream leaving the first cooling phase, which gas stream comprises the feed material and is fed to the dehydrogenation.

In a preferred embodiment of the method according to the invention, it is provided that the second cooling phase is carried out upstream of the first cooling phase. This position relates to the volumetric flow of the feed material. In a further advantageous embodiment of the method according to the invention, it is provided that hydrogen is obtained as a further product material and the hydrogen obtained is at least partially led into a reactor for hydrogen elimination (the dehydrogenation reactor) for stabilization of the hydrogen elimination process.

The hydrogen is preferably obtained by separation of the material mixture, i.e., the gas stream coming from the adsorber.

To achieve the objects mentioned above, in addition to the inventive method, there is provided a device (apparatus) for generating an alkene is provided which is used for the dehydrogenation of a feed material comprising a hydrocarbon and is used for generating a product material which comprises at least one alkene. This device comprises an adsorber for adsorption of water from the stream resulting from the dehydrogenation of a combined gas stream, which combines the feed material with a gas stream which comprises the feed material; a first cooling appliance for cooling a gas stream coming from an adsorber by the gas stream which comprises the feed material, and for cooling the gas stream coming from the adsorber by a condensed component of the gas stream coming from the adsorber in a first cooling phase; a storage appliance for storage of a condensed component of the gas stream coming from the adsorber; and a second cooling appliance for cooling the feed material in a second cooling phase by the condensed component of the gas stream coming from the adsorber. According to the invention the device has an open-loop and/or closed-loop control appliance, with which the volumetric flow of the condensed component of the gas stream coming from the adsorber, which condensed component is to be fed from the storage appliance to the first and/or second cooling phase, can be varied in an automated manner in dependence on the temperature of the gas stream that is leaving the first cooling phase, comprises the feed material, and is fed to the dehydrogenation.

The device according to the invention serves for dehydrogenation of a hydrocarbon and/or for carrying out the method according to the invention.

The adsorber is used for drying the medium flowing through the adsorber.

In addition, the device according to the invention preferably further comprises at least one, and preferably a plurality of, condensation appliances or separators for separating off the condensed component of the gas stream coming from the adsorber.

For taking up the condensate, the respective separator should have a vessel.

The storage volume of the storage appliance is dimensioned in such a manner that the storage appliance can provide sufficient condensate for equalization of the cold transfer fluctuation in the first cooling appliance. The cooling appliances are preferably heat exchangers, wherein the transfer of heat has a cooling action on the medium giving off heat.

That is to say that the open-loop and/or closed-loop control appliance is designed in such a manner that the volumetric flow is controllable automatically thereby. Depending on the temperature of the gas stream leaving the first cooling phase, which gas stream comprises the feed material and is fed to the dehydrogenation, the volumetric flow of condensate is regulated to provided the cooling required in the first and second cooling phases in order to equalize the fluctuations of the adsorber operation and accordingly the fluctuations of the gas stream coming from the adsorber which in turn effect temperature-control fluctuations in the first cooling phase.

The storage appliance can comprise a container and/or a separator for taking up the condensed component of the gas stream coming from the adsorber.

In a heat-efficient embodiment of the device according to the invention, it is provided that the device comprises a heat-insulated space in which the cooling appliances are arranged, wherein the container of the storage appliance is arranged outside this heat-insulated space. Such a heat-insulated space is what is termed a cold box for minimizing the temperature of the fluids flowing through it. On account of the moderate temperature in the container of the storage appliance, there is no necessity to arrange it also in the heat-insulated space. Arranging the container outside the heat-insulated space additionally has the advantage that the heat-insulated space does not need to be constructed with a corresponding volume for taking up the relatively large container. However, for reasons of energy efficiency, likewise arranging the container of the storage appliance in the heat-insulated space should not be ruled out.

To influence the volumetric flow of condensate into the first and/or second cooling phase, the device comprises, in the flow path of the condensed component of the gas stream coming from the adsorber, a pump for transporting the condensate into at least one cooling appliance. Preferably, this pump is arranged downstream of the container of the storage appliance and is therefore also arranged outside the heat-insulated space.

In addition, downstream of the adsorber, or else as a component of the adsorber, a compressor should be arranged for compressing the gas stream coming from the adsorber.

In a further expedient embodiment of the device according to the invention, at least one of the cooling appliances has a mixing appliance for mixing a recycled gas stream with the feed material to form a combined gas stream. The recycle gas stream is a hydrogen gas stream, or a gas stream containing substantially hydrogen, which is formed as a by-product of the product material.

The advantage of the method according to the invention and of the device according to the invention is, in particular, that operating fluctuations of the adsorber can be compensated for by feeding a suitable amount or a suitably dimensioned volume stream of the condensate of the gas coming from the adsorber from a storage container connected downstream of the adsorber into the first and/or second cooling phase. This ensures that the physical parameters of the gas stream to be fed to the dehydrogenation can be kept constant. That is to say, even in the event of temperature fluctuations of the fluid leaving the adsorber, on account of the setting of the flow volumes of condensate fed to the first and/or second cooling phase, the heat exchangers which are conventionally used and dimensioned continue to be usable. There is therefore no necessity, owing to the lower temperature difference possibly being established in the heat exchangers, to arrange larger heat exchangers which are expensive with respect to their production and/or operating costs.

BRIEF DESCRIPTION OF THE DRAWINGS

Further details and advantages of the invention will be illustrated by the FIGURE description hereinafter of an exemplary embodiment shown in the FIGURE, wherein:

FIG. 1 shows a device according to the invention in a schematic presentation.

It can be seen from FIG. 1 that a feed material 1 which can be, e.g., propane, is fed to a system or the device shown. This feed material 1 flows through a second cooling appliance 15, which is preferably constructed as a heat exchanger. Downstream of the branching shown, a first part of the feed material 1 flows, on the one hand, through a first cooling appliance 14, and another part of the feed material, on the other hand, is mixed with a recycle gas stream 4 which, e.g., can comprise substantially hydrogen, in a second mixing appliance 17, which is preferably constructed as a heat exchanger. This mixture is vaporized in this case in the second mixing appliance 17 and conducted further as a gas stream 5, which comprises the feed material, to the first cooling appliance 14.

Before entry into the first cooling appliance 14, the first part of the feed material 1 and the gas stream 5, which comprises the another part of the feed material, are mixed in a first mixing appliance 16 to form a combined gas stream 13. This mixture is vaporized in the course of flowing through the first cooling appliance 14.

The combined gas stream 13 that is generated flows through the reactor 30 in which the combined gas stream 13 is dehydrogenated. The dehydrogenated gas is thereafter passed through the adsorber 40 wherein it is dried and then compressed in the compressor 41. The gas stream 11 coming from the adsorber is again passed through the first cooling appliance 14 where it gives off heat to the combined gas stream 13 and thus heats this fluid. The gas stream 11 coming from the adsorber then arrives in a separator 21 and the vessel 22 thereof, from which the condensed component of the gas stream 12 coming from the adsorber is passed into a container 23. The gas separated off in the separator 21 is passed out as further material 3, which comprises substantially hydrogen. This further material 3 can be used to provide the recycle gas stream 4. In the flow path of the condensed component of the gas stream 12 coming from the adsorber, downstream of the container 23, a pump 50 is arranged which can be operated by an open-loop and/or closed-loop control appliance 60. This pump 50 transports part of the condensed component of the gas stream 12 coming from the adsorber through the first cooling appliance 14 and another part thereof through the second cooling appliance 15, wherein the cold of this medium is given up to the gas stream coming from the adsorber 40 in the first cooling appliance and also to the feed material 1 flowing through the second cooling appliance 15. Thereafter, this fluid leaves the system as product material 2 (which can be sent to a C3 splitter, not shown).

In addition, two flow valves 70, 80, are arranged with which, in each case, the volumetric stream of the condensed component of the gas stream 12 coming from the adsorber to the first cooling appliance 14 and to the second cooling appliance 15 can be set. The open-loop and/or closed-loop control appliance 60 is controllingly connected to the pump 50 and/or the flow valves 70, 80. In particular, the flow valves 70, 80 can be adjustable throttle valves.

The gas leaving the separator 21 is cooled with release of heat in a third cooling appliance 18 for the purpose of heat transfer to the feed material 1 that is passed through this cooling appliance.

In the variant embodiment shown of the device according to the invention, all three cooling appliances 14, 15 and 18 and also the separator 21 and the mixing appliances 16, 17 are arranged in a heat-insulated space. In the embodiment shown heat exchanger 14 and mixing appliance 16 are the same structure, i.e., the heat exchanger is the mixing appliance. The same is true for heat exchanger 18 and mixing appliance 17 in the embodiment shown.

The separator 21, or its vessel 22 that is arranged on the lower side thereof and the container 23 form a storage appliance 20 which is constructed for intermediate storage of the condensed component of the gas stream 12 coming from the adsorber.

During operation of the adsorber 40, or during regeneration thereof, performance fluctuations can occur, in such a manner that the temperature and/or the volume and/or the velocity of the volumetric stream of the gas stream 11 coming from the adsorber varies in such a manner that the heat-insulated space, that is termed the "cold box", can no longer generate sufficient condensate of the gas stream coming from the adsorber 40, and so there is the risk that the combined gas stream 13 does not have the required purity and therefore the dehydrogenation in the reactor 30 cannot be achieved with the desired result. For example, if there is insufficient cooling, this can decrease the purity of hydrogen-containing stream 3, which can in turn lead to a decrease in the purity of recycle gas stream 4. Since recycle gas stream 4 is used to create stream 13, this can also reduce the purity of combined gas stream 13.

In order to avoid this, the pump 50 and/or the flow valves 70, 80, are operated and/or controlled by the open-loop and/or closed-loop control appliance 60 in such a manner that when a deviation is established of a parameter, in particular a physical parameter, of the gas stream 11 coming from the adsorber, from a previously defined limiting value range, more condensed component of the gas stream 12 coming from the adsorber is taken off from the container 23 and/or from the vessel 22 of the separator 21 and fed to the first cooling appliance 14 and/or the second cooling appliance 15, than is necessary during standard operation of the adsorber 40. This means that, despite performance fluctuations of the adsorber 40, a sufficient cooling action is achieved in the first cooling appliance 14 and also the second cooling appliance 15, and consequently no further measures need to be taken for sufficient cooling of the combined gas stream 13, such as, for example, use of larger heat exchangers and/or supplying external cold. Valve 70 regulates the flow of feed material 1 (fresh hydrocarbons) between the two heat exchangers 14 and 18. Therefore, valve 70 regulates the cooling capacity that is provided by the vaporization of the mixture.

Without further elaboration, it is believed that one skilled in the art can, using the preceding description, utilize the present invention to its fullest extent. The preceding preferred specific embodiments are, therefore, to be construed as merely illustrative, and not limitative of the remainder of the disclosure in any way whatsoever.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

The entire disclosures of all applications, patents and publications, cited herein and of corresponding German patent application DE 10 2013 011 984.7, filed Jul. 18, 2013, are incorporated by reference herein.

| List of reference signs | |
|---|---|
| Feed material | 1 |
| Product material | 2 |
| Further material | 3 |
| Recycle gas stream | 4 |
| Gas stream comprising feed material | 5 |
| Heat-insulated space | 10 |
| Gas stream coming from the adsorber | 11 |
| Condensed component of the gas stream coming from the adsorber | 12 |
| Combined gas stream | 13 |
| First cooling appliance | 14 |
| Second cooling appliance | 15 |
| First mixing appliance | 16 |
| Second mixing appliance | 17 |
| Third cooling appliance | 18 |
| Storage appliance | 20 |
| Separator | 21 |
| Vessel | 22 |
| Container | 23 |
| Reactor | 30 |
| Adsorber | 40 |
| Compressor | 41 |
| Pump | 50 |
| Open-loop and/or closed-loop control appliance | 60 |
| First flow valve | 70 |
| Second flow valve | 80 |

The invention claimed is:

1. A method for generating an alkene comprising:
cooling a hydrocarbon-comprising feed stream in a cooling appliance, and then heating said hydrocarbon-comprising feed stream in a further cooling appliance, thereafter subjecting said hydrocarbon-comprising feed stream to dehydrogenation to generate at least one alkene,
removing a gas stream from said dehydrogenation and sending said gas stream from said dehydrogenation to an adsorber,
removing a gas stream from said adsorber and sending said gas stream from said adsorber to said further cooling appliance wherein said gas stream from said adsorber is cooled by said hydrocarbon-comprising feed stream,
removing a cooled gas stream from said further cooling appliance, sending said cooled gas stream to a separator, and removing from said separator a stream of condensed component of said gas stream coming from said adsorber,
splitting said stream of condensed component into a first stream of condensed component and a second stream of condensed component, sending said first stream of condensed component to said cooling appliance to cool said hydrocarbon-comprising feed stream, and sending said second stream of condensed component to said further cooling appliance to cool said gas stream from said adsorber,
wherein the volumetric flows of said first and second streams of condensed component that are fed to said cooling appliance and said further cooling appliance, respectively, are varied in dependence on the temperature of said hydrocarbon-comprising feed stream leaving said further cooling appliance.

2. The method for generating an alkene according to claim 1, wherein said feed material (1) is present as a feed material stream and is mixed with a recycled gas stream (4) to form a combined gas stream (13) which is used as the gas stream comprising feed material in said first cooling phase.

3. The method for generating an alkene according to claim 2, wherein, in the second cooling phase, the feed material (1) is cooled by transfer of cold from the condensed component (12) of the gas stream coming from the adsorber (40) to a feed material stream.

4. The method for generating an alkene according to claim 3, wherein transfer of cold from the gas stream (5), which comprises the feed material, to the gas stream (11) coming from the adsorber and transfer of cold from the condensed component (12) of the gas stream coming from the adsorber (40) to the gas stream (11) coming from the adsorber (40) proceeds in a first heat exchanger, and the transfer of cold from the condensed component (12) of the gas stream coming from the adsorber (40) to the feed material stream proceeds in a second heat exchanger.

5. The method for generating an alkene according to claim 1, wherein, during the operation of said method, the first cooling phase and the second cooling phase, at least partially, are run simultaneously.

6. The method for generating an alkene according to claim 1, wherein, downstream of the adsorber (40), at least one parameter of the material or of the volumetric stream of the gas stream (11) coming from the adsorber (40) is determined, and the at least one determined parameter is compared with a permissible limiting value range and, in the event of deviation of the at least one determined parameter from the limiting value range, at least one parameter of the material and/or of the volumetric stream of the condensed component (12) of the gas stream coming from the adsorber is varied.

7. The method for generating an alkene according to claim 1, wherein the condensed component (12) of the gas stream coming from the adsorber (40) is stored in a storage appliance (20) and from there is fed to the first and/or second cooling phase according to refrigeration performance requirement.

8. The method for generating an alkene according to claim 1, wherein the second cooling phase is carried out upstream of the first cooling phase.

9. The method for generating an alkene according to claim 1, wherein hydrogen is obtained as a further product material (3) and the hydrogen generated is at least partially led into a dehydrogenation reactor (30) for stabilization of the dehydrogenation process.

10. The method for generating an alkene according to claim 1, wherein said gas stream (11) coming from said adsorber (40) is compressed before being cooled in said first cooling phase.

11. The method for generating an alkene according to claim 10, wherein, after being cooled in said first cooling phase, said gas stream (11) coming from said adsorber (40) is sent to a separator (22) wherein it is separated into said condensed component (12) of the gas stream coming from the adsorber (40) and an uncondensed component (2) of the gas stream coming from the adsorber (40).

12. The method for generating an alkene according to claim 11, wherein the condensed component (12) of the gas stream coming from the adsorber (40) is stored in a storage appliance (20) and from there is fed to the first and/or second cooling phase according to refrigeration performance requirement.

13. The method for generating an alkene according to claim 12, wherein the condensed component (12) of the gas stream coming from the adsorber (40) is fed from said storage appliance (20) to said first and second cooling phase as said first stream of a condensed component (12) and said second stream of a condensed component (12), respectively, via a pump.

14. The method for generating an alkene according to claim 13, wherein the volumetric flow of said first stream of a condensed component (12) in said first cooling phase and the volumetric flow of said second stream of a condensed component (12) in said first cooling phase is, in each case, regulated by a control valve.

15. The method for generating an alkene according to claim 14, wherein an open-loop and/or closed-loop control appliance (60) is used to vary the volumetric of said first and second streams of condensed component (12) in an automated manner in dependence on the temperature of the gas stream (5) comprising the feed material leaving said first cooling phase.

16. The method for generating an alkene according to claim 1, wherein said feed material (1) is present as a feed material stream which is first cooled in said second cooling phase, and then divided into a first partial stream and a second partial stream, said second partial stream of said feed stream is combined with a recycle stream to form a combined stream, and then cooled in a third cooling phase by an uncondensed component of the gas stream coming from the adsorber (40), said combined stream is mixed with said first partial stream of said feed stream and the resultant mixed stream is used as the gas stream comprising feed material in said first cooling phase.

* * * * *